US00PP33292P2

(12) United States Plant Patent
Mathey

(10) Patent No.: US PP33,292 P2
(45) Date of Patent: Jul. 27, 2021

(54) ***LAGERSTROEMIA* PLANT NAMED 'SMNLIJ'**

(50) Latin Name: *Lagerstroemia indica*
Varietal Denomination: SMNLIJ

(71) Applicant: Spring Meadow Nursery, Inc., Grand Haven, MI (US)

(72) Inventor: Megan Mathey, Holland, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/115,174

(22) Filed: Dec. 8, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/02; A01H 5/00
See application file for complete search history.

(56) References Cited

PUBLICATIONS https://plantoftheweek.com/2020/10/15/plant-of-the-week-center-stage-crapemyrtle/; Oct. 15, 2020; 4 pages.*
https://springmeadownursery.com/plantfinder/center-stage-coral-49630; Mar. 12, 2021; 1 page.*

* cited by examiner

*Primary Examiner* — Kent L Bell
(74) *Attorney, Agent, or Firm* — Cassandra Bright

(57) ABSTRACT

A new and distinct variety of *Lagerstroemia* plant named 'SMNLIJ' is disclosed, characterized by large coral pink flowers. Plants are upright AND well branched with dark greyed-purple foliage. The new variety is a *Lagerstroemia*, normally used for outdoor ornamental purposes.

3 Drawing Sheets

Latin name of the genus and species: *Lagerstroemia indica.*

Variety denomination: 'SMNLIJ'.

BACKGROUND OF THE INVENTION

The new *Lagerstroemia* cultivar is a product of a planned breeding program conducted by the inventor, Megan Mathey, in Grand Haven, Mich. The objective of the breeding program was to develop ornamental plants with good plant habits and new flower colors. The open pollination resulting in this new variety was made during Summer of 2015.

The seed parent is the unpatented *Lagerstroemia indica* 'Crimson Red'. The pollen parent is unidentified. The new variety was selected in July of 2015 by the inventor in a group of seedlings resulting from the 2015 open pollination, in a commercial nursery in Grand Haven, Mich.

Asexual reproduction of the new cultivar has been performed by softwood cuttings. This was first performed at the same nursery in Grand Haven, Mich. during Summer of 2017, and has shown that the unique features of this cultivar are stable and reproduced true to type in multiple successive generations.

SUMMARY OF THE INVENTION

The cultivar 'SMNLIJ' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNLIJ' These characteristics in combination distinguish 'SMNLIJ' as a new and distinct *Lagerstroemia* cultivar:

1. Attractive dark foliage.
2. Large coral pink blooms.
3. Good branching.
4. Upright plant habit.

PARENT COMPARISON

Plants of the new cultivar 'SMNLIJ' are similar to plants of the seed parent, in most horticultural characteristics; however, plants of the new cultivar 'SMNLIJ' differ in the following;

1. The new variety has coral pink flowers while the seed parent has cherry red flowers.
2. Plants of the new variety produce more branches than the seed parent.
3. The new variety has stronger stems than the seed parent.

COMMERCIAL COMPARISON

Plants of the new cultivar 'SMNLIJ' are comparable to the commercial variety *Lagerstroemia* 'PIILAG-V', U.S. Plant Pat. No. 25,925. The two *Lagerstroemia* varieties are similar in most horticultural characteristics; however, the new variety 'SMNLIJ' differs in the following;

1. Plants of the new variety produce more branches than plants of this comparator.
2. Plants of the new variety are shorter than plants of this comparator.

3. Flowers of the new variety are a more coral shade than the coral pink flowers of this comparator.

BRIEF DESCRIPTION OF THE PHOTOGRAPHS

The accompanying photograph in FIG. 1 illustrates flowering plants outdoors at approximately 3 years old in Grand Haven, Mich.

Figure 1:
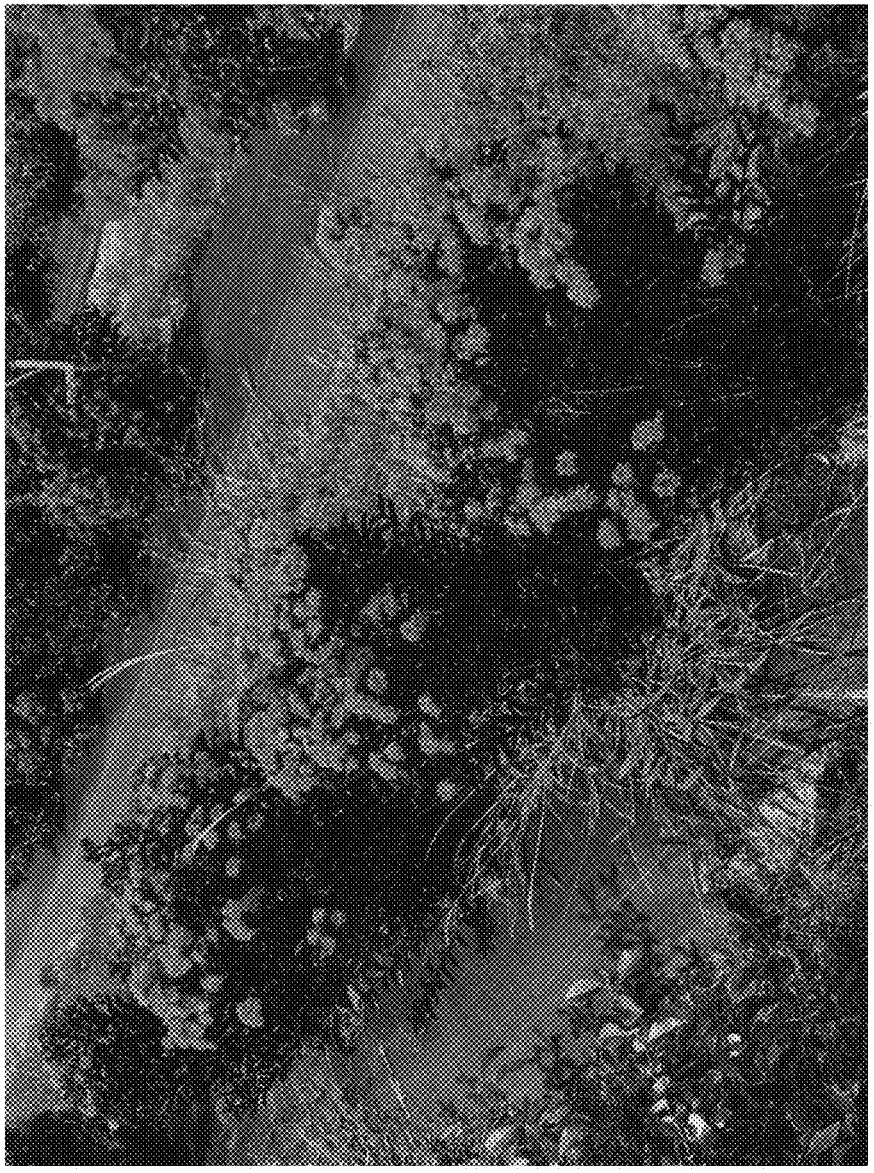
Figure 2:
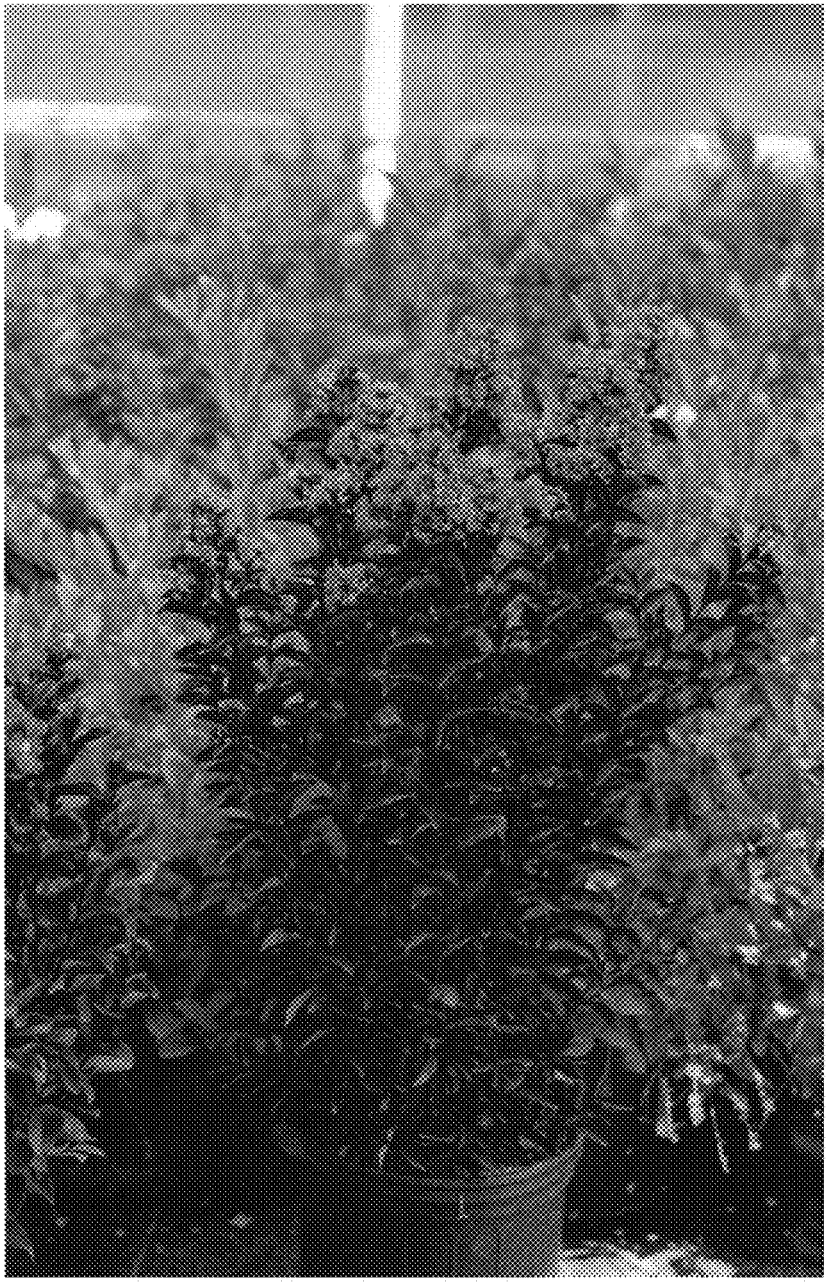
FIG.2 illustrates in full color a typical plant of 'SMNLIJ' in a 3 gallon pot. Age of the plant photographed is approximately 1.5 to 2 years old from a rooted cutting.
Figure 3:
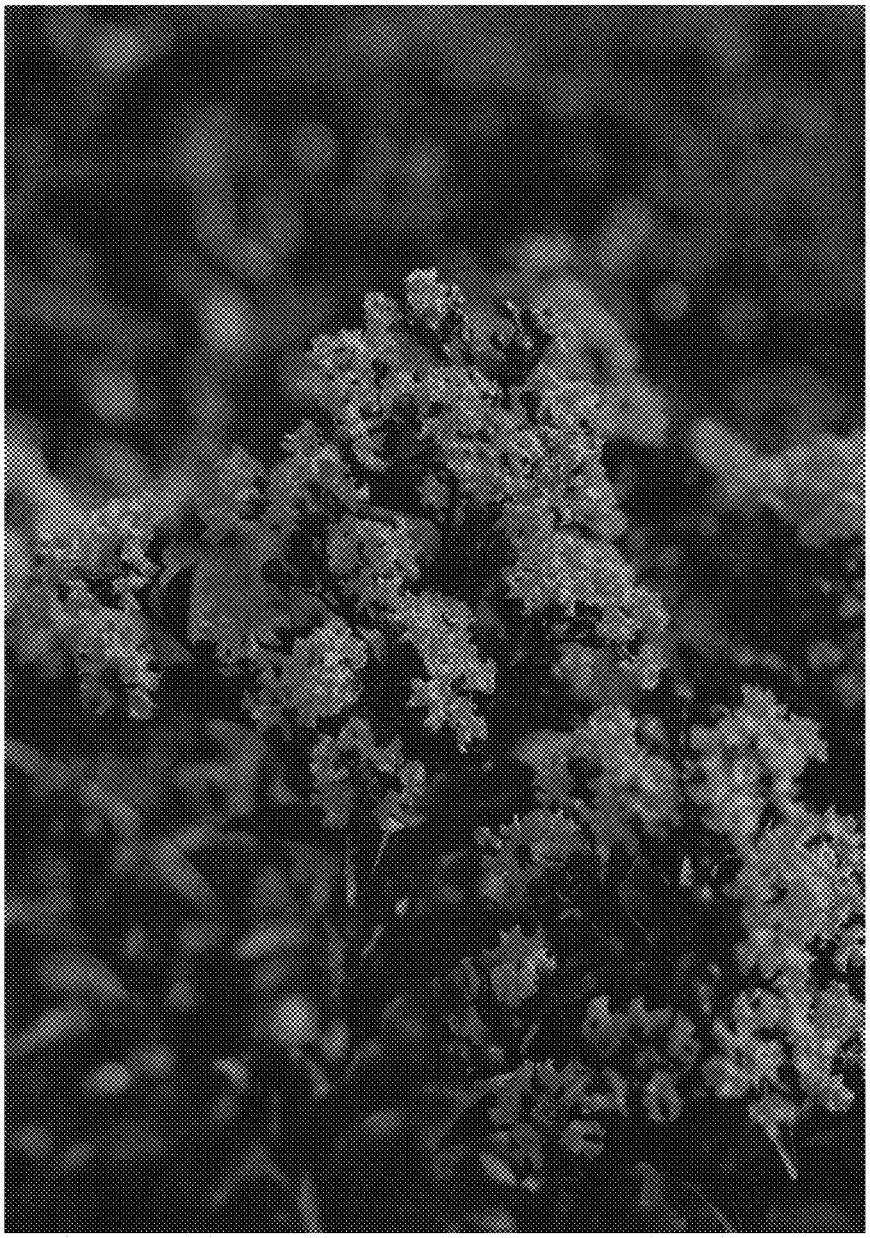
FIG. 3 illustrates a close up of the inflorescence and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNLIJ' plants grown in a poly house in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'SMNLIJ'.

PROPAGATION

Type of propagation typically used: Softwood cuttings.
Time to initiate roots: 21 days at 18-27° C.
Time to produce a rooted cutting: 1-2 months at 18-27° C.
Root description: Thin, dense, fibrous, moderate branching. White in color, not accurately measured with R.H.S. Chart.

PLANT

Age of plant described: 2-3 years old from a rooted cutting.
Container size: 3 gallon container.
Overall plant shape: Upright.
Growth habit: Upright and freely branching. Deciduous flowering shrub.
Plant spread: 64 cm.
Plant height: 48 cm.
Plant vigor: Good.
Length of primary lateral branches: 40 cm.
Diameter of lateral branches: 4 mm.
Quantity of lateral branches: 15.
Stem:
- *Color*.—New growth: RHS Greyed-Purple 187A. Old growth: RHS Greyed-Brown 199C.
- *Shape*.—New growth: Square. Old growth: Round.
- *Strength*.—Good.
- *Aspect angle*.—15-35°.
- *Texture*.—New growth glabrous, old growth woody.

Internode length: Average 2.5 cm.

FOLIAGE

Leaf:
- *Arrangement*.—Sub-opposite.
- *Average length*.—5.5 cm.
- *Average width*.—2.5 cm.
- *Shape of blade*.—Elliptic.
- *Aspect*.—Strong upward fold along center.
- *Apex*.—Acute.
- *Base*.—Obtuse.
- *Margin*.—Entire.
- *Texture of top surface*.—Smooth.
- *Texture of bottom surface*.—Smooth, ribbed.
- *Color*.—Young foliage upper side: RHS Greyed-Purple N186A. Young foliage under side: RHS Brown N200B. Mature foliage upper side: RHS Greyed-Purple N186A. Mature foliage under side: RHS Brown N200B.
- *Venation*.—Type: Pinnate. Venation color upper side: RHS Greyed-Purple N187A. Venation color under side: RHS Greyed-Purple 183C.
- *Petiole*.—Length: 1 mm. Diameter: 1 mm. Texture, upper side: Smooth. Texture, under side: Smooth. Color, upper side: RHS Greyed-Purple 187A. Color, under side: RHS Greyed-Purple 187A.

FLOWER

Natural flowering season: Summer to Fall.
Inflorescence form: Panicle at terminal ends.
Flowers per inflorescence: Average range 20 to 60.
Inflorescence size:
- *Width*.—10 cm.
- *Height*.—16 cm.

Individual flowers:
- *Type*.—Rotate.
- *Habit*.—Whorled upward and outward.
- *Diameter*.—4 cm.
- *Length*.—4 cm.
- *Persistence*.—Self-cleaning.
- *Fragrance*.—Lightly earthy.

Petals:
- *Arrangement*.—Loose whorl of 6 petals.
- *Number*.—6.
- *Shape*.—Undulate orbicular shape.
- *Margin*.—Loose undulate.
- *Tip shape*.—Rounded.
- *Base shape*.—Rounded.
- *Length*.—1.5 cm.
- *Width*.—1.2 cm.
- *Texture*.—Upper: Soft, smooth, delicate. Lower: Soft, smooth, delicate.
- *Color*.—When opening: Upper surface: RHS Red-Purple 58C. Under surface: RHS Red-Purple 58C. Fully opened: Upper surface: RHS Red-Purple 58C. Under surface: RHS Red-Purple 58C.

Bud:
- *Shape*.—Spherical.
- *Length*.—10 mm.
- *Diameter*.—8 mm.
- *Color*.—RHS Greyed-Purple 184A.

Sepals:
*Appearance*.—Smooth, glossy.
*Arrangement*.—Unguiculate.
*Shape*.—Narrowly triangular.
*Tip shape*.—Acute.
*Base shape*.—Obtuse.
*Margin*.—Entire.
*Quantity per flower*.—6.
*Length*.—4 mm.
*Width*.—3 mm.
*Texture*.—Upper: Smooth, coriaceous, rugose. Lower: Smooth.
*Color*.—Upper: Near Greyed-Purple 184A. Lower: RHS Yellow-White 158D.

Calyx:
*Shape*.—Unguiculate.
*Length*.—5 mm.
*Diameter*.—9 mm.

Peduncle:
*Length*.—1.4 cm.
*Diameter*.—2 mm.
*Texture*.—Smooth.
*Color*.—RHS Greyed-Purple 187C.
*Strength*.—Flexible.

Pedicel:
*Length*.—5 mm.
*Diameter*.—1.5 mm.
*Texture*.—Smooth.
*Color*.—RHS Greyed-Purple 187C.
*Strength*.—Flexible.

REPRODUCTIVE ORGANS

Stamens:
*Number*.—About 29.
*Filament length*.—1 cm.
*Filament color*.—RHS Red-Purple 70D, with White 155B at base.

Anthers:
*Shape*.—Linear.
*Length*.—1 mm.
*Color*.—RHS Yellow 9A.
*Pollen*.—Amount: Moderate. Color: RHS Yellow 9A.

Pistil:
*Number*.—1.
*Length*.—2 cm.
*Style*.—Length: 1.8 cm. Color: RHS Greyed-Purple 184D.

Stigma:
*Shape*.—Globular.
*Color*.—RHS Black 202A.
*Ovary color*.—RHS Yellow 11B.

OTHER CHARACTERISTICS

Fruits and seeds: Not observed to date.
Disease/pest resistance: Neither resistance nor susceptibility to normal diseases and pests of *Lagerstroemia* observed.
Temperature range: Observed to tolerate a temperature range from −28° C. to 35° C. Root hardy to −28° C., top of the plant does die back to the ground.

What is claimed is:

1. A new and distinct cultivar of *Lagerstroemia* plant named 'SMNLIJ' as herein illustrated and described.

* * * * *